United States Patent [19]

Jamshidi

[11] Patent Number: 5,593,428
[45] Date of Patent: Jan. 14, 1997

[54] EMERGENCY EXTERNAL CARDIAC DEFIBRILLATOR AND PACING METHOD AND APPARATUS

[75] Inventor: Khosrow Jamshidi, 610 Winston Ct., St. Paul, Minn. 55118

[73] Assignee: Khosrow Jamshidi, St. Paul, Minn.

[21] Appl. No.: 127,200

[22] Filed: Sep. 27, 1993

[51] Int. Cl.⁶ .................................................. A61N 1/39
[52] U.S. Cl. ................................................. 607/10; 607/4
[58] Field of Search ................................. 607/4, 122, 33, 607/5, 115, 10

[56] References Cited

U.S. PATENT DOCUMENTS 4,437,467  3/1984  Helfer et al. .......................... 128/642
4,541,432  9/1985  Molina-Negro et al. ................ 607/46

*Primary Examiner*—William E. Kamm
*Assistant Examiner*—Scott M. Getzow
*Attorney, Agent, or Firm*—Nawrocki, Rooney & Sivertson, P.A.

[57]    ABSTRACT

An emergency external defibrillator and pacing apparatus for applying electrical stimulation to a heart. The apparatus includes a tubular sleeve having an axial passage therethrough, which is insertable through an incision in a chest cavity to a predetermined depth proximate the heart. A first and second electrode is inserted through the axial passage of the sleeve to contact the surface of the heart. Means are provided for applying an electrical current of preset voltage and time interval to selectively stimulate heartbeat and control rhythm. The apparatus electrodes are inserted through an incision in a chest cavity which is held open by the tubular sleeve.

10 Claims, 2 Drawing Sheets

EMERGENCY EXTERNAL CARDIAC DEFIBRILLATOR AND PACING METHOD AND APPARATUS

TECHNICAL FIELD

The present invention relates to medical devices for defibrillating and controlling the rate of a human heart beat. More particularly, it is directed to an emergency external defibrillator and pacing apparatus having a blunt end electrode which is insertable through an incision in the chest cavity of a patient to contact the heart and provide electrical stimulation.

BACKGROUND OF THE INVENTION

Several medical occurrences are well known in which it is necessary to utilize intervention to defibrillate or pace the heartbeat in a human. For example, severe electrical shock may cause the heartbeat to stop or fibrillate. In response, it is necessary to electrically stimulate the heart to restart a normal heartbeat. Many other medical conditions can cause the heartbeat to be irregular. In these instances, a timed electrical pulse is necessary to maintain a constant heartbeat. Many devices have been developed to respond to these conditions.

One type of emergency defibrillation apparatus that is known includes a pair of electrode pads which are placed in contact with the surface or skin on the chest cavity. A strong pulse of current is passed through these electrodes and through the skin and associated tissue to reach the heart muscle, thus stimulating the heartbeat.

A recognized draw back of such a device is the requirement that the current pass through extensive skin, bone, and tissue to reach the heart muscle. This requires the use of a stronger current. Furthermore, the passing of current through a greater portion of the body can cause damage to tissue and organs. These devices are, typically, not able to be utilized to send an electrical pulse at intervals to pace the heartbeat. Rather, these types of devices are only used for restarting the heartbeat after electrical shock, heart attack or other trauma.

External and implantable pacemakers are also well known. Electrical leads are placed in close proximity to the heart during surgery. The pacemaker sends an electrical pulse at predetermined intervals to stimulate the heartbeat in a regular pattern. Such devices, however, are not designed for use in response to an emergency situation.

Accordingly, the need exists for an emergency external defibrillator and pacing apparatus which may be utilized, in response to an emergency, for both functions. The apparatus should include both means for restarting a heartbeat and pacing such heartbeat once initiated. Further, the apparatus should incorporate features which allow personnel to quickly place the electrode in close proximity to the heart muscle. The close proximity of the electrode prevents the need to pass current through other body tissue which may cause damage, and allows timed pulsing of electrical current to maintain a regular heartbeat.

The present invention addresses these needs, as well as other problems associated with existing defibrillation and pacing devices. The present invention also offers further advantages over the prior art and solves problems associated therewith.

SUMMARY OF THE INVENTION

The present invention is an emergency external defibrillator and pacing apparatus for applying electrical stimulation to a human heart. The apparatus is designed for use in response to an emergency situation, such as a heart attack or severe electrical shock in which the heartbeat needs to be reinitiated via inducement of an electrical current pulse. Further, the device is designed for quick insertion proximate a heart muscle so that current need not be passed through other body tissue. Finally, the device also includes features which allow continued timed pulsing of electrical impulses to maintain a standard heartbeat once initiated.

The present invention includes a tubular sleeve having an axial passage therethrough. The sleeve is insertable through an incision in the chest cavity of a patient to a predetermined depth proximate the heart. The sleeve provides access to the heart muscle so that an electrode may be inserted through the axial passage to contact the surface of the heart.

In preferred embodiments, the apparatus of the present invention includes a first electrode having a first end and a second end. The second end includes an electrically conductive exposed blunt end. A second electrode can also be included which has a first end and second end. The second end also has an electrically conductive exposed blunt end.

The second end of the first electrode and the second end of the second electrode can be connected in close proximity to each other to form a single blunt end for insertion through the axial passage of the tubular sleeve proximate the heart.

A first means for applying an electrical current of selected voltage is provided. The first means is connected to the first end of the first electrode. In preferred embodiments, the first means for applying electrical current can include a manually adjustable voltage regulator. The manually adjustable voltage regulator can have a typical range.

The present apparatus can also include a second means for applying an electrical current of selected voltage. Such means is connected to the first end of the second electrode. In preferred embodiments, the second means for applying an electrical current includes a manually adjustable voltage regulator. The second means for applying an electrical current can also include an adjustable timer for pulsing the electrical current at regular intervals. The timer is preferably adjustable between 50 and 80 pulses per minute.

The method for utilizing the above apparatus includes making an incision through the skin of the chest wall of a patient proximate the heart. The tubular sleeve of the apparatus is then inserted through the incision to a predetermined depth proximate the heart muscle. The depth is controlled by the length of the tubular sleeve. The second end of the first and second electrodes is then inserted through the axial passage of the tubular sleeve so that the single blunt end of the combined electrodes contacts the heart muscle. An electrical current can then be applied through either the first or second electrode to stimulate the heartbeat.

In a preferred method, electrical current is pulsed at regular intervals through the second electrode to simulate normal heartbeat rhythm. In this embodiment, the first electrode is then utilized to manually apply an electrical current to the heart muscle in response to loss of heartbeat.

These and various other advantages and features of novelty which characterize the present invention are pointed out with particularity in the claims annexed hereto and forming a part hereof. However, for a better understanding of the invention, its advantages, and the object obtained by its use, reference should be made to the drawings which form a further part hereof, and to the accompanying descriptive matter in which there are illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views.

DETAILED DESCRIPTION OF THE INVENTION

Detailed embodiments of the present invention are disclosed herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one of skill in the art to variously practice the invention.

Figure 1:
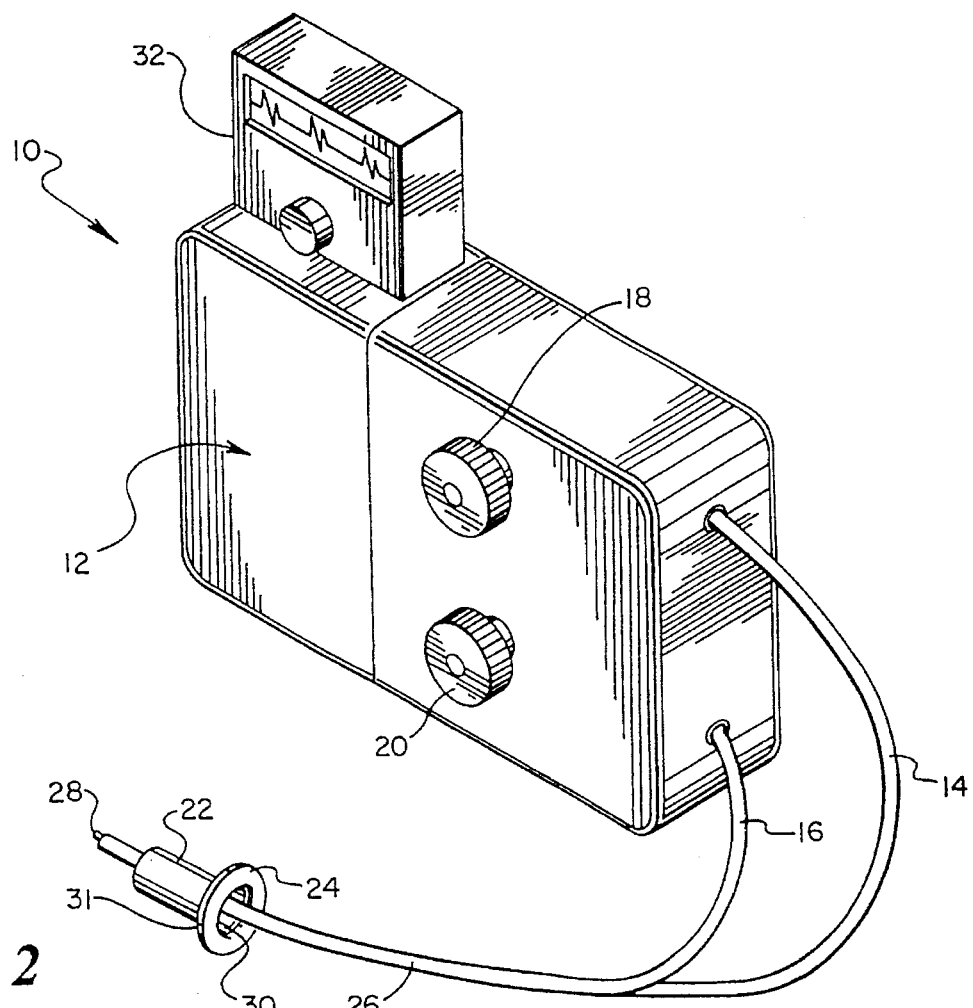
FIG. 1 is a perspective view of an emergency external defibrillator and pacing apparatus of the present invention.

Referring now to FIG. 1, a perspective view of the emergency external defibrillator and pacing apparatus 10 is depicted. A casing 12 encloses a power source. An EKG tracer 32 is also provided for monitoring heartbeat.

Figure 2:
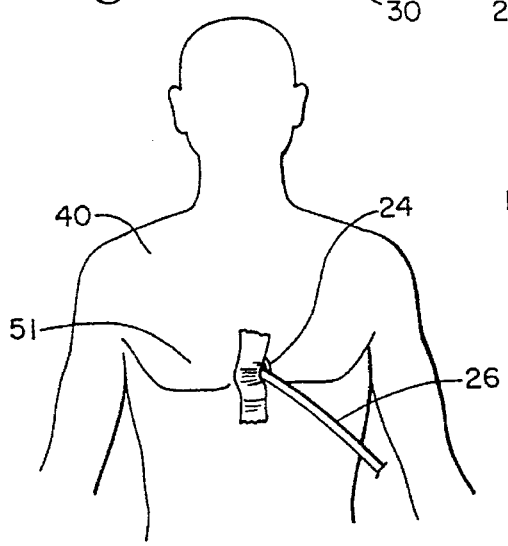
FIG. 2 is an orthographic view depicting the electrode of the present invention inserted in a human patient.
Figure 3:
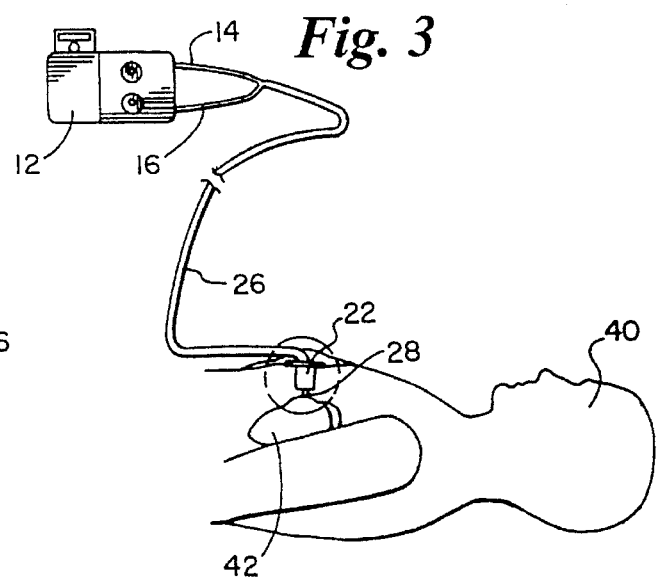
FIG. 3 is an orthographic view of the apparatus showing the location of the tubular sleeve with the lead wire inserted in a patient.

A tubular sleeve 22, having an axial passage 30 therethrough, is included. The tubular sleeve 22, as depicted in FIGS. 2 and 3, is insertable through an incision in the chest cavity 51 of a patient 40 to a predetermined depth proximate the heart 42 of a patient 40.

A first electrode 14 having a first end and second end is also provided. The second end has an electrically conductive exposed blunt end. A second electrode 16 is also provided having a first and second end. The second end of the second electrode 16 also has an electrically conductive exposed blunt end. In a preferred embodiment, the second end of the first electrode 14 and second end of the second electrode 16 are connected in close proximity to form a single blunt end 28, as depicted in FIG. 1, for insertion through the axial passage 30 of the tubular sleeve 22. As best shown in FIG. 1, the electrodes 14, 16 can be joined in an intermediate area to form a single cable 26 enclosing the first electrode 14 and second electrode 16.

The tubular sleeve 22 is preferably manufactured from a biocompatible, non-conductive material. In a preferred embodiment, the tubular sleeve 22 includes a flange 24 on one end. The flange 24 has an annular surface 31 generally perpendicular to the axial passage 30. The annular surface 31 is in planar contact with the surface of the chest cavity 51 of a patient 40 when the tubular sleeve 22 is inserted in the chest cavity 51. Flange 24 fixes the depth to which the tubular sleeve 22 is insertable into the patient 40, thus providing a safeguard against contact of the heart muscle 42 by the sleeve 22.

A first means for applying electrical current of selected voltage is also included. The first means is adjusted by control knob 18 and is connected to the first end of the first electrode 14. In a preferred embodiment, the first means for applying electrical current includes a manually adjustable voltage regulator. The manually adjustable voltage regulator has a typical range of voltages available. In use, the first electrode and the means for adjustment are utilized to reinitiate a heartbeat that has ceased.

A second means for applying an electrical current of selected voltage, adjusted by control knob 20, is also provided. The second means is connected to the first end of the second electrode 16. In a preferred embodiment, the second means for applying an electrical current also includes a manually adjustable voltage regulator. The second means for applying an electrical current further includes an adjustable timer for pulsing the electrical current at regular intervals. In a preferred embodiment, the adjustable timer can be adjusted between 50 and 80 pulses per minute. In use, the second electrode 16 and associated equipment is utilized for pacing the heartbeat via timed electrical impulses, once the heartbeat has been reinitiated using the first electrode 14.

Figure 4:
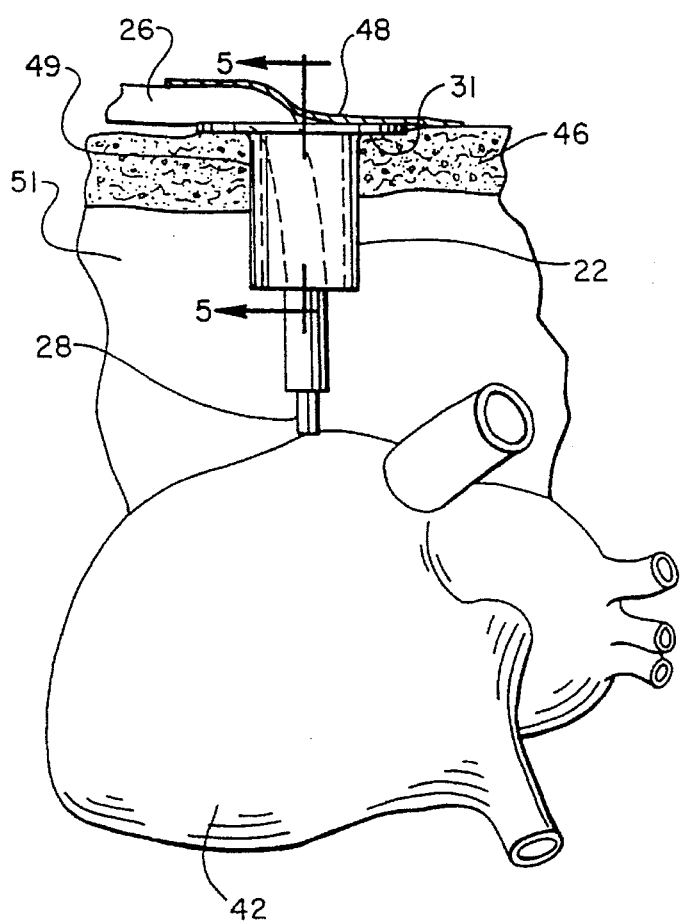
FIG. 4 is a cross-sectional view illustrating in detail the tubular sleeve inserted into the chest cavity and the electrode of the invention through the tubular sleeve to contact the heart muscle.
Figure 5:
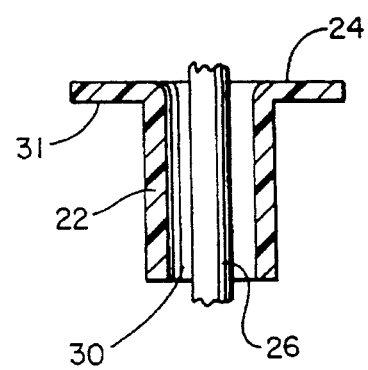
FIG. 5 is a cross-sectional view of the tubular sleeve of FIG. 4 taken generally along line 5—5.

Next referring to FIGS. 4 and 5, the details of the electrode blunt end 28, in contact with the heart 42, passing through the tubular sleeve 22 are illustrated. These features are best described in conjunction with the method of utilizing the present invention.

An incision 49 is first made through the skin 46 of the chest cavity 51. The tubular sleeve 22 is then inserted through the incision 49. The depth of insertion is controlled by the flange 24 which contacts the surface of the skin 46. Access is thus provided to the chest cavity for insertion of the electrode single cable 26 and blunt end 28.

The electrode single cable 26 is inserted through the axial passage 30 of the tubular sleeve 22. The electrode single cable 26 is inserted until the single blunt end of the electrode 28 comes into contact with the heart 42. It is also believed that the present apparatus will function with the blunt end 28 in close proximity with the heart muscle 42 without actually contacting the heart. Tape 48 is utilized to hold the electrode 26 in place when inserted.

An electrical current is then applied to the single blunt end 28 through either the first electrode 14 or second electrode 16. In a preferred method, as previously disclosed, the electrical current is pulsed at regular intervals through the second electrode 16 to simulate normal heartbeat rhythm. An electrical current is manually applied when necessary to the first electrode 14 in response to a loss of heartbeat.

New characteristics and advantages of the invention covered by this document have been set forth in the foregoing description. It will be understood, however, that this disclosure is, in many respects, only illustrative. Changes may be made in details, particularly in matters of shape, size, and arrangement of parts, without exceeding the scope of the invention. The scope of the invention is, of course, defined in the language in which the appended claims are expressed.

What is claimed is:

1. An emergency external defibrillator and pacing apparatus for applying an electrical current to a heart, said apparatus comprising:

a. a tubular sleeve having an axial passage therethrough, said sleeve insertable through an incision in a chest cavity to a predetermined depth proximate said heart;

b. a first electrode having a first end and second end, said second end having an electrically conductive exposed blunt end;

c. a second electrode having a first end and a second end, said second end having an electrically conductive exposed blunt end, said second end of said first electrode and said second end of said second electrode connected in close proximity to form a single blunt end for insertion through said axial passage of said tubular sleeve proximate said heart;

d. first means for applying an electrical current of selected voltage, said first means connected to the first end of said first electrode; and e. second means for applying an electrical current of selected voltage, said second means connected to the first end of said second electrode.

2. The emergency external defibrillator and a pacing apparatus of claim 1, wherein said tubular sleeve is constructed from an electrically non-conductive material.

3. The emergency external defibrillator and pacing apparatus of claim 2, wherein said tubular sleeve has a first end and a second end, said first end having a flange thereon with a radial surface generally perpendicular to said axial passage, said radial surface adapted to be in planar contact with the surface of said chest cavity when said tubular sleeve is inserted in said chest cavity.

4. The emergency external defibrillator and pacing apparatus of claim 1, wherein said first means for applying an electrical current includes a manually adjustable voltage regulator.

5. The emergency external defibrillator and pacing apparatus of claim 1, wherein said second means for applying an electrical current includes a manually adjustable voltage regulator.

6. The emergency external defibrillator and pacing apparatus of claim 5, wherein said second means for applying an electrical current includes an adjustable timer for pulsing said electrical current at regular intervals.

7. The emergency external defibrillator and pacing apparatus of claim 6, wherein said adjustable timer can be adjusted between 50 and 80 pulses per minute.

8. A method for defibrillating and pacing a heartbeat of a human heart comprising the steps of:

a. providing an emergency external defibrillator and pacing apparatus which includes, (1) a tubular sleeve having an axial passage therethrough;

(2) a first electrode having a first end and second end, said second end having an electrically conductive exposed blunt end;

(3) a second electrode having a first end and a second end, said second end having an electrically conductive exposed blunt end, said second end of said first electrode and said second end of said second electrode connected in close proximity to form a single blunt end;

(4) first means for applying an electrical current of selected voltage, said first means connected to the first end of said first electrode; and (5) second means for applying an electrical current of selected voltage, said second means connected to the first end of said second electrode;

b. making an incision through the skin of the chest wall of a patient proximate said heart;

c. inserting said tubular sleeve through said incision to a predetermined depth proximate said heart, said depth controlled by the length of said tubular sleeve;

d. inserting the second end of said first and second electrodes through the axial passage of said tubular sleeve so that said single blunt end contacts said heart;

e. applying an electrical current to said single blunt end through said first or second electrode to stimulate said heartbeat.

9. The method of claim 8 wherein said electrical current is pulsed at regular intervals through said second electrode to simulate normal heartbeat rhythm.

10. The method of claim 8, wherein the emergency external defibrillator and pacing apparatus provided in accordance with step a. further includes:

(6) manual means for controlling said first means for applying an electrical current of selected voltage;

and wherein said electrical current application is manually controlled through said first electrode in response to loss of heartbeat.

* * * * *